(12) United States Patent
Edwards

(10) Patent No.: US 9,819,847 B1
(45) Date of Patent: Nov. 14, 2017

(54) UNIFORM LIGHTING OF SURFACES FOR VISUAL INSPECTION

(71) Applicant: Excelis Inc, McLean, VA (US)

(72) Inventor: Kevin E. Edwards, Fincastle, VA (US)

(73) Assignee: Harris Corporation, Melbourne, FL (US)

(*) Notice: Subject to any disclaimer, the term of this patent is extended or adjusted under 35 U.S.C. 154(b) by 284 days.

(21) Appl. No.: 14/702,948

(22) Filed: May 4, 2015

(51) Int. Cl.
G06K 9/00 (2006.01)
H04N 5/225 (2006.01)
G01N 21/88 (2006.01)
H04N 5/232 (2006.01)

(52) U.S. Cl.
CPC ....... *H04N 5/2256* (2013.01); *G01N 21/8851* (2013.01); *H04N 5/232* (2013.01); *H04N 2005/2255* (2013.01)

(58) Field of Classification Search
CPC ................ G06T 7/0004; G06T 7/0001; G06T 2207/30148; G06T 2207/30164; G01N 21/88; H04N 5/2256
See application file for complete search history.

(56) References Cited

U.S. PATENT DOCUMENTS

| | | | |
|---|---|---|---|
| 4,328,532 A | 5/1982 | Smith | |
| 5,309,277 A * | 5/1994 | Deck | H01S 5/4025 250/205 |
| 5,325,276 A | 6/1994 | Sullivan | |
| 5,745,308 A * | 4/1998 | Spangenberg | G01N 15/1436 359/381 |
| 6,056,420 A * | 5/2000 | Wilson | F21K 9/00 362/230 |
| 6,565,231 B1 * | 5/2003 | Cok | F21S 6/002 313/504 |
| 7,139,016 B2 * | 11/2006 | Squilla | A61B 1/00048 348/65 |
| 7,639,861 B2 | 12/2009 | Michael et al. | |
| 7,676,137 B2 | 3/2010 | Schick et al. | |
| 8,016,199 B2 | 9/2011 | Nunnink | |

FOREIGN PATENT DOCUMENTS

JP    2005322602 A    11/2005

* cited by examiner

*Primary Examiner* — Amir Alavi
(74) *Attorney, Agent, or Firm* — Edell, Shapiro & Finnan LLC

(57) ABSTRACT

A fixture retains a housing in a fixed position relative to an imaging device. The housing has an aperture through which a surface recessed into the housing is aligned with the imaging device by the fixture. A planar electroluminescent illuminator is held in the fixture within a pocket of the fixture in which the housing is received. The illuminator uniformly emits light in response to electrical power applied thereto and the illuminator has an aperture formed therein held in alignment by the fixture with the aperture in the housing such that the light emitted by the illuminator is directed towards the recessed surface. An imaging device generates an image of the recessed surface through the aperture in the housing and the aperture in the illuminator.

16 Claims, 5 Drawing Sheets

RELATED ART

_US 9,819,847 B1_

UNIFORM LIGHTING OF SURFACES FOR VISUAL INSPECTION

TECHNICAL FIELD

The present disclosure relates to illumination for purposes of visual inspection and/or machine vision of reflective surfaces including such surfaces that are recessed into a housing or mount.

BACKGROUND

Proper illumination of surfaces for purposes of visual inspection presents a number of challenges, particularly when the surfaces to be inspected are recessed and reflective, such as in the case of an image intensifier tube screen optic. Conventional commercially available light sources such as ring lamps, hemispherical reflecting illuminators, grazing illuminators, panel illuminators, ambient light sources, scanned laser, etc., do not uniformly illuminate surfaces, particularly when the surface is recessed, sufficiently for camera-based image analysis. The commercially available light sources fail due to hot spots of intensity formed on the reflective surface, because light from such sources cannot be directed sufficiently into recesses to prevent shadows on the surface being inspected, large size of such sources prevents proper lighting of small structures received in test fixtures, physical spacing requirements work outside of short focal camera operation, etc. Accordingly, research and development of lighting systems that overcome these shortfalls is ongoing.

SUMMARY

A fixture retains a housing in a fixed position relative to an imaging device. The housing has an aperture through which a surface recessed into the housing is aligned with the imaging device by the fixture. A planar electroluminescent illuminator is held in the fixture within a pocket of the fixture in which the housing is received. The illuminator uniformly emits light in response to electrical power applied thereto and the illuminator has an aperture formed therein held in alignment by the fixture with the aperture in the housing such that the light emitted by the illuminator is directed towards the recessed surface. An imaging device generates an image of the recessed surface through the aperture in the housing and the aperture in the illuminator.

DESCRIPTION OF EXAMPLE EMBODIMENTS

Figure 1A:
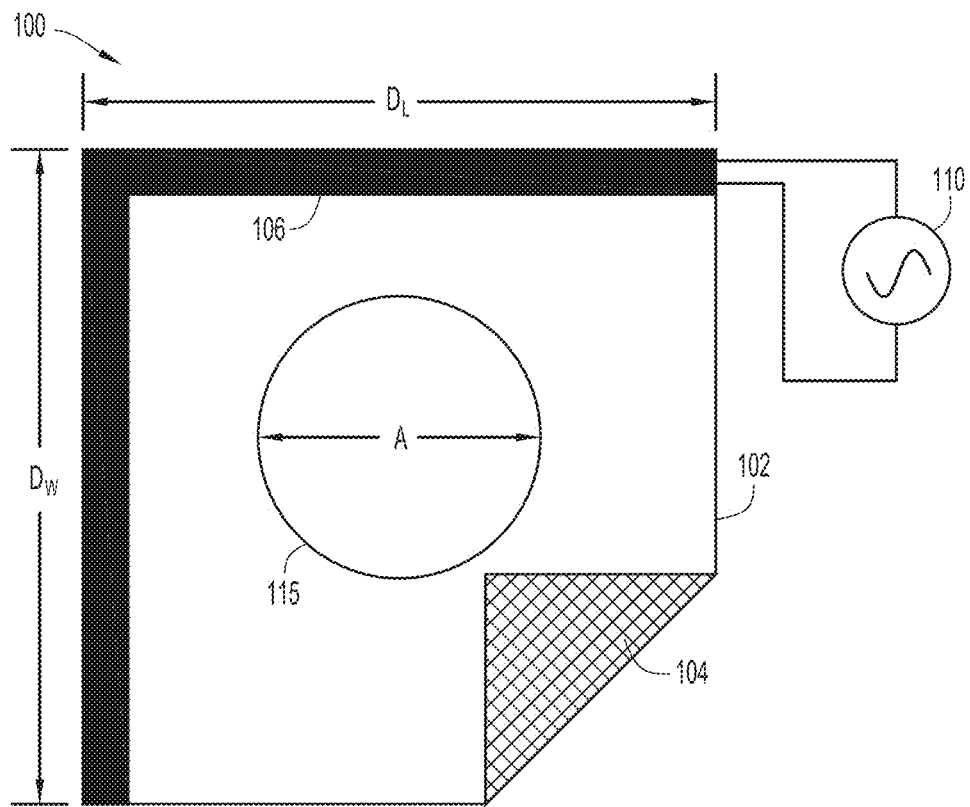
FIGS. 1A-1B are illustrations of a planar illuminator used in embodiments the present general inventive concept.

The present inventive concept is best described through certain embodiments thereof, which are described in detail herein with reference to the accompanying drawings, wherein like reference numerals refer to like features throughout. It is to be understood that the term invention, when used herein, is intended to connote the inventive concept underlying the embodiments described below and not merely the embodiments themselves. It is to be understood further that the general inventive concept is not limited to the illustrative embodiments described below and the following descriptions should be read in such light.

Additionally, the word exemplary is used herein to mean, "serving as an example, instance or illustration." Any embodiment of construction, process, design, technique, etc., designated herein as exemplary is not necessarily to be construed as preferred or advantageous over other such embodiments.

Additionally, mathematical expressions are contained herein and those principles conveyed thereby are to be taken as being thoroughly described therewith. It is to be understood that where mathematics are used, such is for succinct description of the underlying principles being explained and, unless otherwise expressed, no other purpose is implied or should be inferred. It will be clear from this disclosure overall how the mathematics herein pertain to the present invention and, where embodiment of the principles underlying the mathematical expressions is intended, the ordinarily skilled artisan will recognize numerous techniques to carry out physical manifestations of the principles being mathematically expressed.

The figures described herein include schematic block diagrams illustrating various interoperating functional modules. Such diagrams are not intended to serve as electrical schematics and interconnections illustrated are intended to depict signal flow, various interoperations between functional components and/or processes and are not necessarily direct electrical connections between such components. Moreover, the functionality illustrated and described via separate components need not be distributed as shown, and the discrete blocks in the diagrams are not necessarily intended to depict discrete electrical components.

The techniques described herein are directed to uniform lighting to a recessed mounted concave surface overcoming lighting reflections, non-uniform lighting, shadowing and artifacts that adversely affect manual and machine vision inspection of the surface. This invention allows for automated inspection of applicable surfaces. Upon review of this disclosure and appreciation of the concepts disclosed herein, the ordinarily skilled artisan will recognize other visual inspection contexts in which the present inventive concept can be applied. The scope of the present invention is intended to encompass all such alternative implementations.

FIG. 1A depicts an exemplary illuminator 100 that can be used in conjunction with embodiments of the present invention. Illuminator 100 is a planar component of dimensions $D_L \times D_w$ comprising a light emitting surface 102 and a backing surface 104. It is to be understood that the present invention is not limited to a particular size, which will vary by application. In certain embodiments of the invention, each of $D_L$ and $D_w$ is a few centimeters.

Figure 1B:
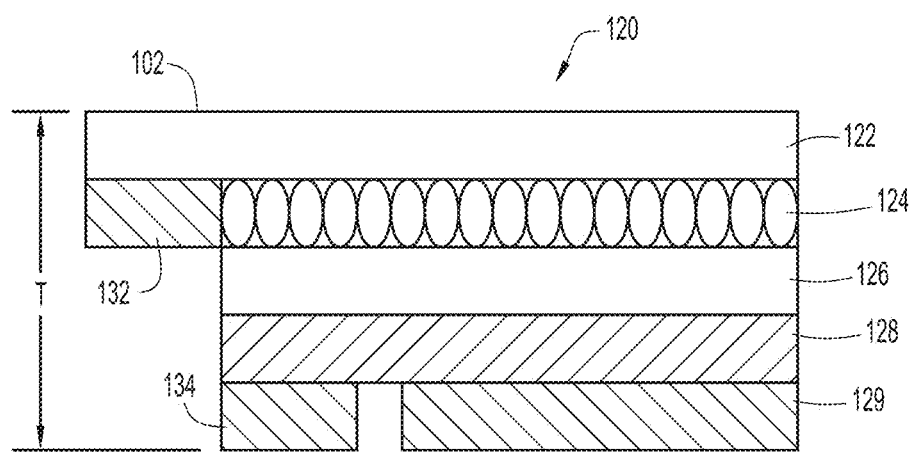

FIG. 1B is a cross-sectional view of an exemplary electroluminescent film (ELF) 120 from which illuminator 100 may be constructed. ELF 120 is comprised of several layers: a translucent upper electrode layer 122, a luminescent layer 124, an insulating layer 126, a lower electrode layer 128 and an opaque backing layer 129. ELF 120 may include contacts 132 and 134 that may be connected to power source 110 and may be disposed on the periphery of illuminator 100 as power bus 106. A voltage of a predetermined voltage level and frequency applied across contacts 132 and 134 causes luminescent layer 124 to emit light at a corresponding intensity. In certain embodiments, light intensity is varied by modifying one or both of the voltage level and frequency. The thickness T of ELF 120 may be no greater than 0.5 mm.

As illustrated in FIG. 1A, illuminator 100 may have an imaging aperture 115 formed therein through which a surface under inspection may be imaged. The diameter A of the aperture may be sized appropriately based on particular imaging requirements of the application, e.g., the aperture size of the imaging device for a particular illumination level, focal length of the imaging device to the surface being imaged, etc.

Figure 2:
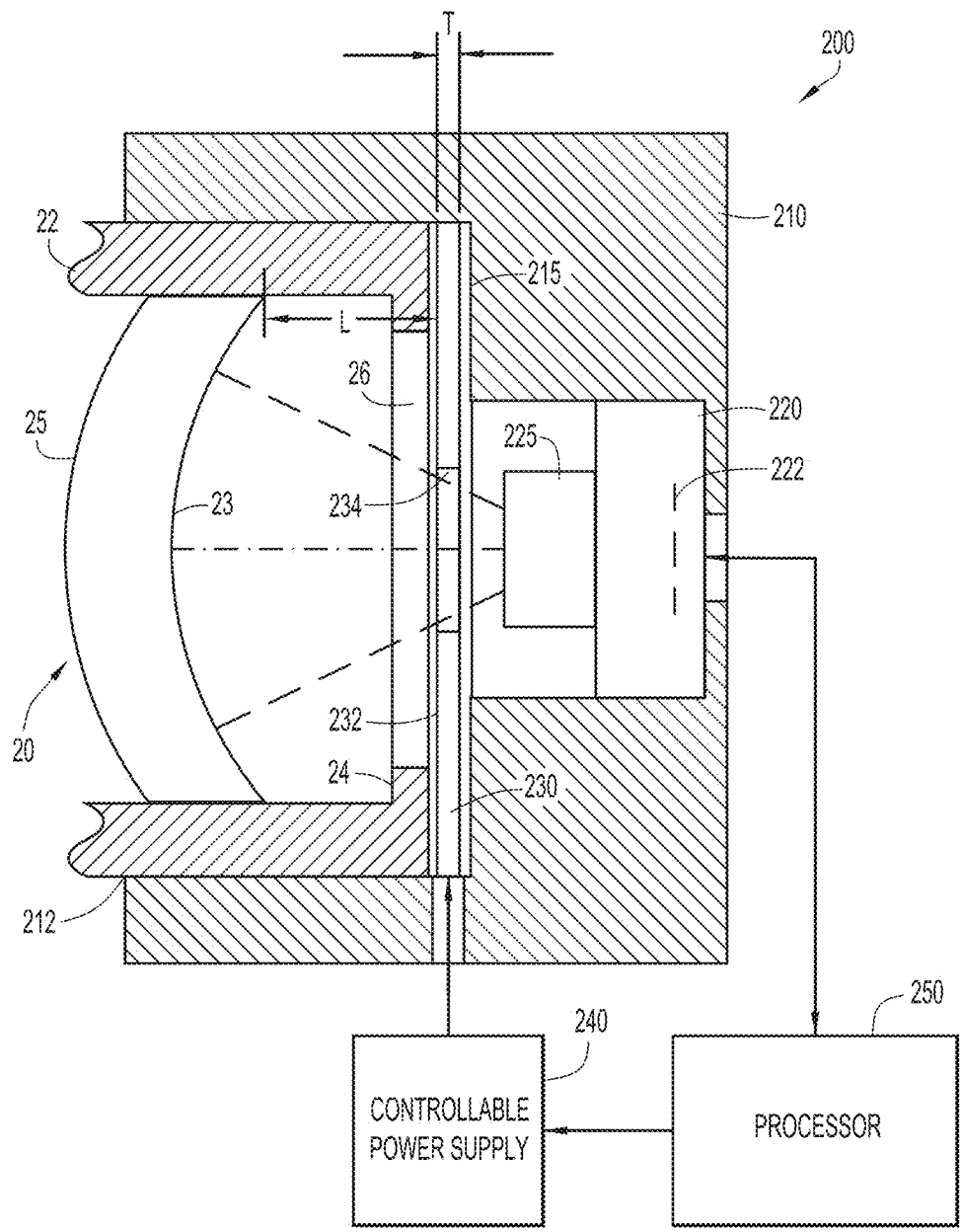
FIG. 2 is a schematic block diagram of an inspection fixture by which the present general inventive concept can be embodied.

FIG. 2 is a schematic block diagram of an exemplary inspection system 200 by which the present invention can be embodied. It is to be understood that for purposes of explanation and not limitation, inspection system 200 is illustrated in simplified form; implementations of inspection system 200 may be more complex and may contain components other than those illustrated in the figure. Upon review of this disclosure, those having skill in the art will recognize numerous configurations in which inspection system 200 can be realized without departing from the spirit and intended scope of the present invention.

Inspection system 200 includes an inspection fixture 210 having a pocket 212 into which a component under test (CUT) 20 is received. For purposes of explanation and not limitation, exemplary CUT 20 includes a housing such as optical tube 22 in which an optical component 25 is retained a distance L from a face of end stop 24. An aperture 26 may be formed in endstop 24 through which a surface 23 of optical component 25 is exposed. In the illustrated example, optical component 25 is a concave component having a predetermined reflectivity, the surface 23 of which is to be inspected.

Exemplary inspection system 200 may include an imaging device 220, such as a camera, by which an image of surface 23 is generated. Imaging device 220 may include optics 225 by which light reflected from surface 23 is collected and conveyed onto an image plane 222 of imaging device 220. A charge-coupled device (CCD) or complementary metal-oxide-semiconductor (CMOS) device or similar digital image capture device (not illustrated) may be situated on the image plane 222 and image data collected thereby may be provided to processor 250. In certain embodiments, imaging device 220 implements autofocus mechanisms by which surface 23 is maintained within focus of imaging device 220. Additionally, imaging device may be configured for short distance, close focus.

Exemplary inspection system 200 includes a thin (e.g., T≤0.5 mm) illuminator 230 installed in a pocket 212 of fixture 210. Illuminator 230 may be held against the terminal wall 215 of pocket 212 in a suitable way, such as by an adhesive or in grooves formed in fixture 210 (not illustrated), such that light emitting surface 232 is directed away from terminal wall 215. Illuminator 230 may have a aperture 234 formed therein that is sized to provide maximal illumination into optical tube 22 through aperture 26, while allowing maximal exposure to imaging device 220.

Figure 3:
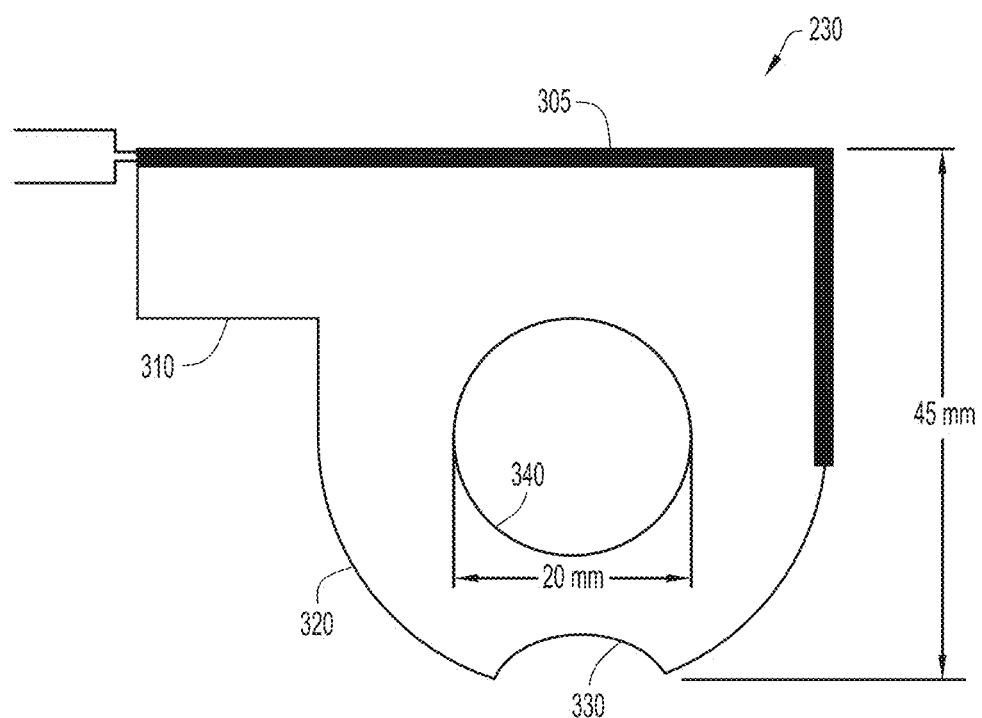
FIG. 3 is a planar illuminator utilized in the inspection fixture of FIG. 2.

An exemplary illuminator 230 is illustrated in FIG. 3, which may be fabricated from ELF, such as that illustrated in FIG. 1B. Accordingly, illuminator 230 may be made small, e.g., 45 mm and no greater than 0.5 mm thick. Illuminator 230 may have a circularly shaped region 320 matching the shape of pocket 212, as well an extension portion 310 on which connection to electrical bus 305 is afforded. Aperture 340 may be formed to be concentric with circularly shaped region 320 so as to be coaxial with the optics of imaging device 220 as well as with aperture 26 in optical tube 22. Additionally, a cutout portion 330 may be formed in illuminator 230 to accommodate non-planar or otherwise irregular features on endstop 24. For example, when CUT 20 is an image intensifier tube (where optical component 25 is a view screen of the image intensifier tube), cutout 330 may be formed to accommodate electrical contacts extending from optical 22 through which electrical power is provided to the image intensifier tube. ELF may be fabricated in shapes other than that illustrated in FIG. 3 per the requirements of the application in which the present invention is embodied.

Returning to FIG. 2, processor 250 may perform various functions for inspection system 200. For example, processor 250 may ingest images of surface 23 from imaging device 220 and may display such images on a user interface (not illustrated) implemented by processor 250. When so embodied, a user may inspect surface 23 for defects from the images displayed on the user interface. In another embodiment, processor 250 may implement various image processing techniques by which surface defects are detected and highlighted in a suitable manner to be brought to the attention of human users. Those having skill in machine vision inspection will recognize various techniques that can be used for such purpose without departing from the spirit and intended scope of the present invention.

Inspection system 200 may include a controllable power supply 240 communicatively coupled to processor 250. Processor 250 may be configured to alter the illumination on surface 23 automatically or under manual operation by a user. Processor 250 may provide suitable control signals to controllable power supply 240 in accordance with illumination requirements at any given time. In turn, controllable power supply 240 may provide electrical power to illuminator 230, such as on power bus 305.

Figure 4A:
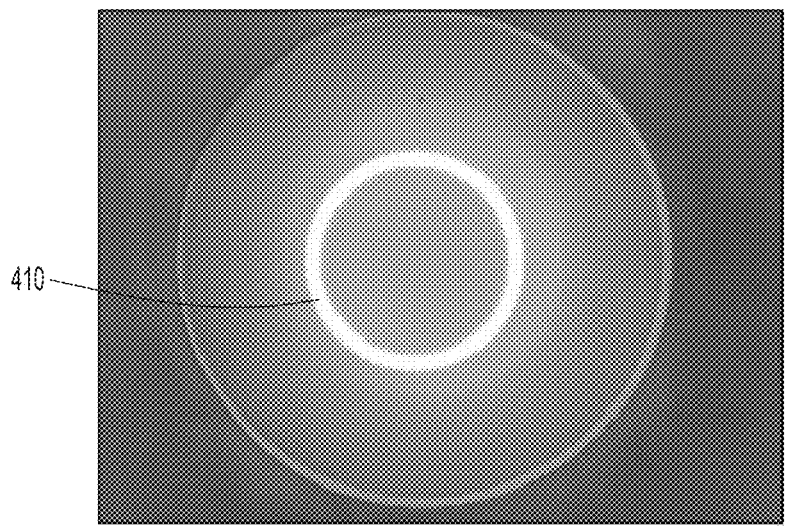
FIGS. 4A-4B are illustrations that compare conventional illumination with that of embodiments of the present general inventive concept.
Figure 4B:
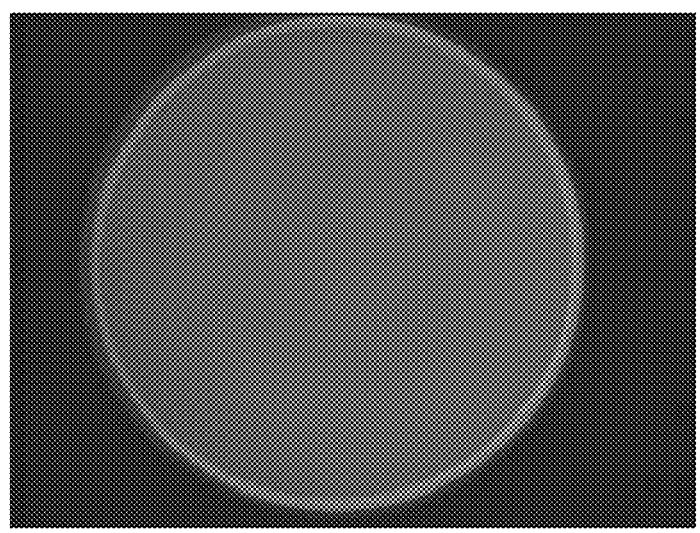

FIG. 4A is an illustration of a surface inspection image illuminated by a conventional ring lamp and FIG. 4B is an illustration of a surface inspection image illuminated by an ELF illuminator constructed in accordance with the present invention. For both images, the imaged surface is a recessed concave surface of an image intensifier tube viewing screen. As illustrated in the figure, ring lamp illumination (FIG. 4A) produces a bright ring reflection 410 that can not only overwhelm or otherwise hide defects in the bright region, but may also interfere with autofocussing of the imaging device. Uniform illumination (FIG. 4B) overcomes problems that are encountered with conventional ring lamps to improve the detection capability, both manual and automatic, of the inspection system.

Figure 5:
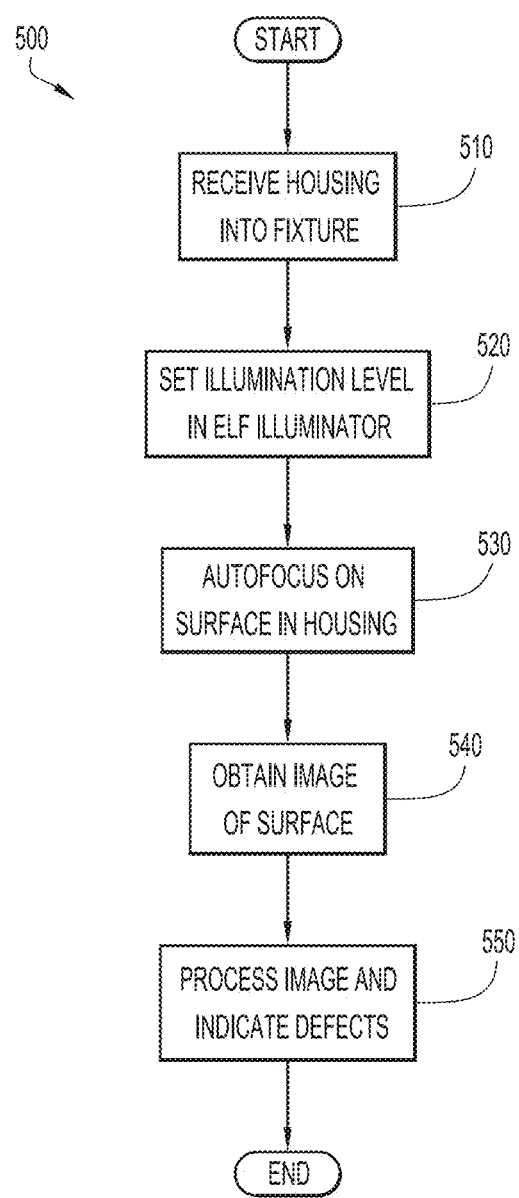
FIG. 5 is a flow diagram of a recessed surface inspection process by which the present invention can be embodied.

FIG. 5 is a flow diagram of an exemplary inspection process by which the present invention can be embodied. In operation 510, a housing (e.g., optical tube 22) in which the surface to be inspected is contained is received into an inspection fixture (e.g., fixture 210). In operation 520, the illumination level (intensity) is set in the ELF illuminator, such as by establishing the appropriate electrical power characteristics (e.g., by processor 250) in a power supply (e.g., controllable power supply 240), and providing the electrical power to the power bus of the ELF. In operation 530, the imaging device (e.g., imaging device 220) may autofocus on the surface in the housing and, in operation 540, an image of the surface is obtained from the imaging device, such as by processor 250. In operation 550, the image is processed and defects on the inspected surface, should there be any, are indicated, such as on a user interface.

Certain embodiments of the present general inventive concept provide for the functional components to manufactured, transported, marketed and/or sold as processor instructions encoded on computer-readable media. The present general inventive concept, when so embodied, can be practiced regardless of the processing platform on which the processor instructions are executed and regardless of the manner by which the processor instructions are encoded on the computer-readable medium.

It is to be understood that the computer-readable medium described above may be any non-transitory medium on which the instructions may be encoded and then subsequently retrieved, decoded and executed by a processor, including electrical, magnetic and optical storage devices. Examples of non-transitory computer-readable recording media include, but not limited to, read-only memory (ROM), random-access memory (RAM), and other electrical storage; CD-ROM, DVD, and other optical storage; and magnetic tape, floppy disks, hard disks and other magnetic storage. The processor instructions may be derived from algorithmic constructions in various programming languages that realize the present general inventive concept as exemplified by the embodiments described above.

The descriptions above are intended to illustrate possible implementations of the present inventive concept and are not restrictive. Many variations, modifications and alternatives will become apparent to the skilled artisan upon review of this disclosure. For example, components equivalent to those shown and described may be substituted therefore, elements and methods individually described may be combined, and elements described as discrete may be distributed across many components. The scope of the invention should therefore be determined not with reference to the description above, but with reference to the appended claims, along with their full range of equivalents.

What is claimed is:

1. An imaging system to image a surface recessed into a housing having an aperture through which the surface is exposed, the imaging system comprising:
   an imaging device to generate an image of the recessed surface through the aperture in the housing;
   a fixture having a pocket to retain the housing in a fixed position relative to the imaging device;
   an electroluminescent illuminator within the pocket of the fixture to uniformly emit light in response to electrical power applied thereto, the illuminator having an aperture formed therein held in alignment by the fixture with the aperture in the housing such that the light emitted by the illuminator is directed towards the recessed surface, enabling the image device to autofocus on the recessed surface; and
   a power supply to provide the electrical power to the illuminator at a user selectable level or frequency that establishes intensity of the light emitted by the illuminator.

2. The imaging system of claim 1, wherein the illuminator is fabricated from a planar electroluminescent film.

3. The imaging system of claim 2, wherein the electroluminescent film is no greater than 0.5 mm thick.

4. The imaging system of claim 1, wherein the imaging device is a camera.

5. The imaging system of claim 4, wherein the camera is a digital image capturing camera.

6. The imaging system of claim 5, wherein the camera contains at least one of a charge-coupled device and a complementary metal-oxide-semiconductor image sensor.

7. The imaging system of claim 4, further comprising: a processor configured to execute a surface inspection process to indicate defects on the surface.

8. The imaging system of claim 7, wherein the camera is an autofocus camera.

9. A method of imaging a surface recessed into a housing having an aperture through which the surface is exposed, the method comprising:
   receiving the housing into a fixture such that the aperture therein is aligned with an imaging device;
   illuminating the surface by an electroluminescent illuminator having an aperture formed therein that is aligned with the aperture in the housing, the illuminator emitting uniformly distributed light about the aperture;
   providing electrical power to the illuminator that establishes the illumination level;
   autofocusing by the imaging device on the illuminated surface; and
   obtaining an image of the illuminated surface by the imaging device.

10. The method of claim 9, further comprising:
    determining an illumination level for the image.

11. The method of claim 9, further comprising:
    determining by a processor whether a defect is present on the surface; and
    indicating, in the image, the location of the defect on the surface.

12. The method of claim 9, wherein illuminating the surface includes illuminating the surface by a planar electroluminescent film.

13. The method of claim 12, wherein the planar electroluminescent film is no greater than 0.5 mm thick.

14. The method of claim 9, wherein the imaging device is a camera.

15. The method of claim 14, wherein the camera is a digital image capturing camera.

16. The method of claim 15, wherein the digital image capturing camera contains at least one of a charge-coupled device and a complementary metal-oxide-semiconductor image sensor.

* * * * *